US00RE38919E

(19) United States
(12) Reissued Patent
Garrido et al.

(10) Patent Number: US RE38,919 E
(45) Date of Reissued Patent: Dec. 13, 2005

(54) INJECTABLE MICROFOAM CONTAINING A SCLEROSING AGENT

(75) Inventors: Juan Cabrera Garrido, Granada (ES); Juan Cabrera Garcia-Olmedo, Granada (ES)

(73) Assignee: BTG International Limited, London (GB)

(21) Appl. No.: 10/458,806

(22) Filed: Jun. 11, 2003

Related U.S. Patent Documents

Reissue of:
(64) Patent No.: 5,676,962
Issued: Oct. 14, 1997
Appl. No.: 08/407,595
Filed: Feb. 23, 1995

U.S. Applications:
(63) Continuation of application No. PCT/ES94/00064, filed on Jun. 21, 1994.

(51) Int. Cl.[7] ..... A61F 2/01
(52) U.S. Cl. ..... 424/423; 424/422; 424/484
(58) Field of Search ..... 424/423, 484, 424/422, 424, 425; 604/82 C, 507

(56) References Cited

U.S. PATENT DOCUMENTS

| | | | | |
|---|---|---|---|---|
| 3,698,453 | A | | 10/1972 | Morane et al. |
| 3,970,219 | A | | 7/1976 | Spitzer et al. |
| 4,019,657 | A | | 4/1977 | Spitzer et al. |
| 4,040,420 | A | | 8/1977 | Speer |
| 4,127,131 | A | | 11/1978 | Vaillancourt |
| 4,276,885 | A | | 7/1981 | Tickner et al. |
| 4,292,972 | A | | 10/1981 | Pawelchak et al. |
| 4,466,442 | A | * | 8/1984 | Hilmann et al. |
| 4,718,433 | A | | 1/1988 | Feinstein |
| 5,064,103 | A | | 11/1991 | Bennett |
| 5,084,011 | A | | 1/1992 | Grady |
| 5,141,738 | A | | 8/1992 | Rasor et al. |
| 5,542,935 | A | | 8/1996 | Unger et al. |
| 5,623,085 | A | | 4/1997 | Gebhard et al. |
| 5,656,200 | A | | 8/1997 | Boettcher et al. |
| 5,676,962 | A | | 10/1997 | Garrido et al. |
| 5,902,225 | A | | 5/1999 | Monson |
| 6,561,237 | B1 | | 5/2003 | Brass et al. |

FOREIGN PATENT DOCUMENTS

| | | | |
|---|---|---|---|
| CA | 1 232 837 | | 2/1988 |
| DE | 3048744 | A1 | 7/1982 |
| DE | 3050812 | C2 | 3/1985 |
| DE | 8704600.8 | | 11/1987 |
| DE | 3417182 | C2 | 1/1989 |
| DE | 69418286 | T2 | 10/1999 |
| EP | 0 054 728 | A1 | 6/1982 |
| EP | 0 077 752 | | 4/1983 |
| EP | 0 123 235 | | 10/1984 |
| EP | 0 131 540 | | 1/1985 |
| EP | 0 217 582 | A2 | 4/1987 |
| EP | 324938 | * | 7/1989 |
| EP | 0 324 938 | A1 | 7/1989 |
| EP | 0 359 246 | | 3/1990 |
| EP | 0 656 203 | A1 | 6/1995 |
| EP | 0 997 396 | A1 | 5/2000 |
| ES | 2 068 151 | | 4/1995 |
| FR | 1 547 768 | | 11/1968 |
| FR | 2 672 038 | | 7/1992 |
| FR | 2 775 436 | | 9/1999 |
| WO | WO 92/05806 | * | 4/1992 |
| WO | WO 95/00120 | | 1/1995 |
| WO | WO 96/25194 | | 4/1996 |
| WO | WO 99/43371 | | 9/1999 |
| WO | WO 00/24649 | | 5/2000 |
| WO | WO 00/66274 | | 11/2000 |
| WO | WO 00 72821 | A1 | 12/2000 |

OTHER PUBLICATIONS

Jan–Christoph G.R. Wollmann, MD, "The History of Sclerosing Foams", Dermatol Surg. vol. 30, No. 5, pp. 694–703, May 2004.
German Nullity Action; English Translation of the Reply to appeal dated Feb. 12, 2004.
DVD #1 and #2 containing video clips shown during interview of Jan. 7, 2004.
Written commentary tracking the DVDs submitted herein.
R. Bayeux, "Comparative Resistance of Dog and Rabbit to Intravenous Injection of Oxygen", Compt. Rend. vol. 156, pp. 1329–1331, 1913, with Abstract in English.
F.W. Runnicliffe et al., "The Intravenous Injection of Oxygen Gas as a Therapeutic Measure", Lancet, vol. II, pp. 321–323, 1916, with Abstract in English.
G. Galata, "Intravenous Injection of Oxygen in Dogs", Archivio di Fisiologia, vol. 21, pp. 331–350, 1923, with Abstract in English.
E.J. Orbach, "Schlerotherapy of Varicose Veins", American Journal of Surgery, vol. LXVI, No. 3, pp. 362–366, Dec. 1944.
R. E. Weston et al., "The Influence of Denitrogenation on the Response of Anesthetized Dogs to Intravenously Injected Oxygen", vol. 26, pp. 837–848, 1946.
A. Lemaire et al., "Effect of Intra–arterial oxygen injection on blood cholesterol", Therapie, vol. 13, pp. 395–399, 1958, with Abstract in English.
V. Gorisch et al., "Expiration of labeled oxygen after intravenous insufflation", Medicina Experimentalis, vol. 1, pp. 333–338, 1959, Abstract in English.
V. Gorisch et al., "Appearance of intravenously given radioactive oxygen in expired air", Naunyn–Schmiedebergs Archiv fuer Experimentelle Pathologie und Pharmakologie, vol. 238, pp. 106–107, 1960, with Abstract in English.
I. Singh, "Life Without Breathing", Arch. int. Pharmacodyn., vol. CXXXVII, No. 3–4, pp. 318–330, 1962.

(Continued)

*Primary Examiner*—Jyothsna Venkat
(74) *Attorney, Agent, or Firm*—Finnegan, Henderson, Farabow, Garrett & Dunner, LLP

(57) ABSTRACT

Injectable microfoam for sclerotcraphy. The sclerotherapy of varices is based on the injection of liquid substances capable of suppressing them. The present invention relates to the preparation of sclerosing substances in the form of a microfoam. The microfoam is prepared with sclerosing agents, and is then injected in the vein to be treated, so that the microfoam displaces the blood contained in the vein and provides for the contact of the sclerosing agent with the vascular endothelium, with a predetermined known concentration and during a controllable time.

16 Claims, No Drawings

OTHER PUBLICATIONS

E. J. Orbach, "The Place of Injection Therapy in the Treatment of Venous Disorders of the Lower Extremity—with Comments on its Technique", Presented at the Annual Meeting of the International College of Angiology, London, pp. 18–23, Jul. 1965.
S. Efuin et al., "Oxygen Parameters of Blood and Tissues during Intravascular Oxygenation of the Organism", Eksperimental'naya Khirurgiya I Anesteziologiya, vol. 5, pp. 183–186, 1974, with Abstract in English.
B. Ya Varshavskii, "Mechanism of Changes in Renal Activity Following intravenous oxygen", vol. 53, No. 2, pp. 173–177, 1967, with Abstract in English.
S. Efuin et al., Oxygen Parameters of Blood and Tissues during Intravascular Oxygenation of the Organism, Eksperimental'naya Khirurgiya I Anesteziologiya, vol. 5, pp. 71–74, 1974, with Abstract in English.
F.B. Cockett, "Arterial Complications during Surgery and Sclerotherapy of Varicose Veins", Phlebology, vol. 1, pp. 3–6, 1986.
L. Karmazsin et al., "Experimental Study of Lipid Peroxidation Following Intravenous Oxygen", Kiserletes Orvostudomany, vol. 39, pp. 342–348, 1987, with Abstract in English.
R. M. Knight et al., "Ultrasonic Guidance of Injections into the Superficial Venous System", Phlebology, pp. 339–341, 1989.
Z.B. Shafi et al., "Factors Affecting High Shear Preparation of Albumin Microspheres", Pharmaceutical Sciences Research GRoup, p. 144P, 1990.
G. Miserey et al., "Sclerose Sous Echographie Dans Certaines Zones a Risques", Phlebologie, vol. 44, No. 1, pp. 85–96, 1991.
M. Schadeck et al., "Echotomographie de la Sclerose", Phlebologie, vol. 44, No. 1, pp. 111–130, 1991.
R. de Somer–Leroy et al., "Echographie du Creux–Poplite Recherche D'Une Arteriole Petite Saphene Avant Sclerotherapie", Phlebologie, vol. 44, No. 1, pp. 69–78, 1991.
Vin, "Echo–Sclerotherapy of the Small Saphenous Vein", Phlebologie, vol. 44, No. 1, pp. 79–84, 1991 with Abstract in English.
P. Thibault et al., "Recurrent Varicose Veins", Phlebology, vol. 18, pp. 895–900, 1992.
K. Biegeleisen et al., "Inadvertent Intra–Arterial Injection Complicating Ordinary and Ultrasound–Guided Sclerotherapy", Phlebology, vol. 19, pp. 953–958, 1993.
German Nullity Action Complaint filed Jul. 27, 2001 and translation into English.
German Nullity Action First Brief filed Dec. 3, 2001 and translation into English.
German Nullity Action Supplemental Brief filed Dec. 31, 2002 and translation into English.
German Nullity Action Kreusler Brief filed Jan. 27, 2003 and translation into English.
German Nullity Action Decision by German Court in English dated Feb. 4, 2003.
German Nullity Action English Translation of the Substantiation of Appeal to the Federal Court of Justice on Sep. 26, 2003.
K1—Von P. Flückiger, "Nicht–operative retrograde Varicenverödung mit Varsylschaum", Schweizerische Medizinische Wochenschrift, No. 48, pp. 1368–1370, (1956) with English translation.
K2—H. Mayer et al., "On the aetiology and treatment of varices of the lower extremities", Angiology, Chirurgische Praxis, pp. 521–528, (1957) with English translation.
K3—Meyers'Encyclopedia, 5$^{th}$ Edition, vol. 15, pp. 386 (1985) with English translation.
K4—Von P. Flückiger et al., "Beitrag sur Technik der ambulanten Varizenbehandlung", No. 12, pp. 617–621, Mar. 23, 1963.
K5—Dr. Med. Jože Baridevic; "Varicosclerozation in Phlebological Practice"; The Journal for Doctors, in Clinical and Practice; XXI vol. No. 3, pp. 126–136; Jan. 11, 1989, and translation into English.
K6—W. Gillesberger; "The Equipment of the Dermatologist Working in the Field of Phlebology", the Journal for Skin Diseases; vol. 44 (18), pp. 669–674; 1969 and translation into English.
K7—Dr. E. Lunkenheimer; Letter to Chem. Fabrik Kreussler & Co.; Mar. 20, 1967 and translation into English.
K8—Gianni Belcaro; "Micro–sclerotherapy"; Sclerotherapy in Venous Disease; pp. 89–95; 2002.
K9—M. Schadeck; "Ultrasound–controlled Sclerotherapy of the Great Saphenous Veins"; Phlébologie; vol. 46, No. 4, pp. 673–682, 1993 and tranlsation into English.
K10—E. Rabe et al.; "Guidelines to Sclerosing Treatment of Varicose Veins"; Leitlinien der DGP, Phlebologie; vol. 6, pp. 154–158; 2001 and translation into English.
K11—DE 3417182 C2 and EP 0 054 728 and translations into English.
K12—K. Sigg, "Newer Aspects of the Technique of Treating Varicosities", Therpeutishce Umschau, vol. 6, pp. 127–134, 1949 and translation into English.
K13—M. Schadeck; "Duplex Controlled Sclerosing Treatment of the Great Saphenous Vein"; Phlebol; vol. 25, pp. 78–82; 1996 and translation into English.
K14—R. Rowden–Foote; "Varicose Veins Hemorrhoids and Other Conditions—Their Treatment by Injection"; London, H.K. Lewis & Co. Ltd.; pp. 13–45, 106–119; 1944.
K15—A. Ree; "The Treatment of Varicose Veins with Etamolin Foam"; Acta Dermato–Venereologica; vol. 39, pp. 428–432; 1959.
K16—E.J. Orbach et al.; "The Thromobogenic Property of Foam of a Synthetic Anionic Detergent (Sodium Tetradecyl Sulfate N.N.R.)", Angiol 1, pp. 237–243; 1950.
K17—M.D.H.–D. Bock; "Varicosis and its Therapy"; Ärztliche Praxis; XIX vol., No. 60, pp. 2146–2148; Jul. 29, 1967 and translation into English.
K18—O. Henschel;"Die Varizenverördening—Verördungstherapie mit Aethoxysklerol—Kreussler"; p. 22; 1968 and translation into English.
K19–13 Pr. Dr. rer. nat. Reinhard Höhler ; "The Expression <<Micro Foam>> is Neither Generally Known to Experts in the Field nor Well–defined"; Laboratoire de Physique de Milieux Diviséet Interfaces Université de Marne–la–Vallée and translation into English.
K20—Chronologia der Schaumverödung.
K21—J. Orbach, "Sclerotherapy of varicose Veins", American Journal of Surgery, vol. LXVI, No. 3, pp. 362–366, Dec. 1944.
K22—J.R. Cabrera Garrido et al., "Extending the Limits of Sclerotherapy: New Sclerosing Products", Phlébp;pgoe, vol. 50, No. 2, pp. 181–188, 1997.
K23—J. Cabrera; "Application Techniques for Sclerosant in Micro–Foam Form"; pp. 39–44.

K24—Video (VHS) tape of Compression Sclerotherapy, H.R., Bernbach, M.D. and English Translation of the Documentation Accompanying the Video K24; pp. 1–16.
K25—Dr. J.C. Wollmann et al.; Evaluation of the Test; Kreussler Pharma; pp. 17–28, Jan. 29, 2003.
K26—Pr. Dr. R. Höhler ; "The Indication of the Rotation Speed and the Duration of the Rotation is not Sufficient for Foams Produced by a Rotating Brush to be Able to Produce a Foam that Has Well–Defined Properties and that Can Be Reproduced."; and translation into English.
K27—Pr. Dr. R. Höhler; "Comparison Between Three–Dimensional Foams and Two–Dimensional Foams Which Are Produced by Squashing a Three–Dimensional Foam between a Two–Dimensional Foam."; Laboratoire de Physique de Milleux Divisés et Interfaces Université de Marne–la–Vallée and translation into English.
Meyers's Encyclopedia 5$^{th}$ Edition, 1895, vol. 15, pp. 386.
L. Moszkowiez, "Treatment of Varicose Veins with Sugar Injections, combined with vein ligation", Zentralblatt fur Chirurgie, No. 28, pp. 1731–1736, 1927 and translation into English.
G. de Takats, "Ambulatory Ligation of the Saphenous Vein", The Journal of the American Medical Association, vol. 94, No. 16, pp. 1194–1197, Apr. 19, 1930.
G. de Takats et al., "The Injection Treatment of Varicose Veins", Surgery, Gynecology and Obstetrics, vol. L, No. 3, pp. 545–561, Mar. 1930.
De L'Academie des Sciences, Conformement A Une Decision de L'Academie, pp. 890–892, Jan. 1930 and translation into English.
I.S. Tunick et al., "Sodium Morrhuate as a Sclerosing Agent in the Treatment of Varicose Veins", Annals of Surgery, vol. XCV, pp. 734–737, 1932.
H. Jausion, "Glycerine Chromee et Sclerose des Ectasies Veineuses", La Presse Medicale, No. 53, pp. 1061–1063, Jul. 5, 1933.
H. Harkins et al., "Embolism by Air and Oxygen: Comparative Studies", Proceedings of the Society for Experimental Biology and Medicine, vol. 32, pp. 178–181, 1934–35.
L. Ferguson, "Ligation of Varicose Veins, Ambulatory Treatment Preliminary to Sclerosing Injections", Annals of Surgery, vol. CII, pp. 304–314, 1935.
A. Ochsner et al., "Comparative Value of Intravenous Sclerosing Substances", Archives of Surgery, vol. 29, No. 3, pp. 397–416, Sep. 1934.
H. Biegeleisen, "Fatty Acid Solutions for the Injection Treatment of Varicose Veins", Annals of Surgery, vol. CV, pp. 610–615, 1937.
A. Schmler, "Clinical Comparison of Sclerosing Solutions in Injection Treatment of Varicose Veins, Delayed Slough: Recurrence of Varices", The American Journal of Surgey, vol. XXXVI, No. 1, pp. 389–398, Apr. 1937.
R.M. Moore et al., "Injections of Air and Carbon Dioxide into a Pulmonary Vein", Annals of Surgery, vol. 112, pp. 212–218, 1940.
W. Heyerdale et al., "Management of Varicose Veins of the Lower Extremities", Annals of Surgery, vol. 114, pp. 1042–1049, 1941.
R. Rowden–Foote; "Varicose Veins Hermorrhoids and Other Conditions—Their Treatment by Injection"; London, H.K. Lewis & Co. Ltd.; pp. 13–45, 106–119; 1944.
E.J. Orbach; "Sclerotherapy of Varicose Veins—Utilization of an Intravenous Air Block"; American Journal of Surgery; vol. LXVI, No. 3, pp. 362–366; Dec. 1944.
L. Reiner, "The Activity of Anionic Surface Active Compounds in Producing Vascular Obliteration", Surface Active Sclerosing Agents, Proceedings of the Society for Experimental Biology and Medicine, vol. 62, pp. 49–54, May–Jun. 1946.
R. Zingg, "Experimental tests with the new sclerosing agent "Geigy"", pp. 1–9, 1948.
R. Foote, "Treatment", Varicose Veins, Chapter 5, p. 65 and 86, 1949.
K. Sigg, "Newer Aspects of the Technique of Treating Varicosities", Therapeutishce Umschau, vol. 6, pp. 127–134, 1949 and translation into English.
R. Jung, "Injection Treatment of Varicose Veins", Praxis, 195–198, 1950 and translation into English.
E. J. Orbach, "Contributions to the Therapy of the Varicose Complex", Journal of the International College of Surgeons, pp. 765–771, Jun. 1950.
H. Rogge, "On the dangers of sclerosing recurring varicose veins", Deutsche Medizinische Wochenschrift, No. 9, p. 301, 1950 and translation into English.
E.J. Orbach et al.; "The Thrombogenic Property of Foam of a Synthetic Anionic Detergent (Sodium Tetradecyl Sulfate N.N.R.)", Angiol 1, pp. 237–243; 1950.
Sigg, "Regarding treatment of varicose veins and their complications", Dermatologica, vol. 100, p. 317, 1950 and translation into English.
G. de Takats et al., "Division of the Popliteal Vein In Deep Venous Insufficiency of the Lower Extremities", Society for Vascular Surgery Issue, vol. 29., No. 3, pp. 342–354, Mar. 1951.
R.S. Handley, "The Treatment of Varicose Veins", The Practitioner—Diseases of the Veins, No. 993, vol. 166, pp. 228–235, Mar. 1951.
H.E. Lockhart–Mummery et al., "Varicose Ulcer—A Study of the Deep Veins with Special Reference to Retrograde Venography", The British Journal of Surgery, vol. XXXVIII, No. 151, pp. 284–295, Jan. 1951.
M. Mairano, "Metodo combinato chirurgico–sclerosante o metodo sclerosante semplice nel trattamento delle varici essenziali?" Minerva Chirugica, vol. VI, No. 16, pp. 244–247, May 1951.
E. Orbach, "Leg Ulcers of Vascular Origin and Their Therapy" The American Journal of Surgery, vol. LXXXI, No. 5, pp. 568–572, May 1951.
M. Battezzati et al., "Treatment of Lower Limb Varices with Multiple Endermic Ligations and Sclerosant Injections Combined or not with Stripping of the Long Saphenous Vein's higher region", Minerva Chirurgica, pp. 936–939, 1952 and translation into English.
H. Leonhardt, "On the Treatment of Extensive Formation of Varicose Veins with Ligature of the v. Saphena and Varicoid Injection Through Ditally Inserted Ureteral Catheter", Ärztliche Wochenschrift, vol. 7, No. 3, pp. 56–58, Jan. 1952 and translation into English.
G. Mayer, "The Treatment of Varicose Veins from the point of View of Sclerotherapy, in particularly on the Basis of Varicophtine", Münchener Medizinische Wochenschrift, vol. 16, No. 20, Columns 1037–1039, Jan. 1952 and translation into English.
H.G. Oden, "Can the Results of the Treatment of Varicose Vains and Ulcus Cruris be Improved?", Münchener, Medizinische Wochenschrift, vol. 22, No. 8, pp. 364, Jan. 1952 and translation into English.

P. Piulaches et al., "Pathogenic Considerations on Varicose Veins Developed in Pregnancy", Lyon Chirurigical, Bulletin official de la Socirte de Chriurgie de Lyon, vol. 47, No. 3, pp. 263–278, Apr. 1952 and translation into English.
P. Jaeger, "The Current Treatment Standard for Crural Ulcer and Varices", Deutsche Medizinische Wochenschrift, vol. 77, No. 14, pp. 421–425, Apr. 4, 1952 and translation into English.
K. Sigg, "The Treatment of Varicosities and Accompanying Complications", Angiology, The Journal of Vascular Diseases, vol. 3, No. 5, pp. 355–379, Oct. 1952.
H. Wefers et al., "Results of Injection Treatment with Regard to Extreme Varication", Zentralblatt für Chirurgie, Issue No. 43, pp. 1825–1828, 1952 and translation into English.
K. Sigg, "The Foamed Rubber Compression for Phlebitis and for Phlebitic and Varicose Complications", Die Medizinische, No. 27–28, pp. 910–915, Jul. 1952 and translation into English.
P. Plulachs et al., "Pathogenic Study of Varicose Veins", Angiology, The Journal of Vascular Diseases, vol. 4, No. 1, pp. 59–100, Feb. 1953.
F. Kunkel, "Medical Journal of Munich", 95$^{th}$ year of edition, vol. 30, No. 44, pp. 53 1953 and translation into English.
Von Hans Brücke et al., "The combined foam sclerosis of varices", Wiener Medizinische Wochenschrift, vol. 104, No. 1, pp. 111–113, Jan. 1954 and translation into English.
G. de Takats et al., "Aneurysms: General Considerations", Angiology, The Journal of Vascular Disease, vol. 5, No. 3, pp. 173–208, Jun. 1954.
A. Hauser et al., "Prophylaxis of Phlebitis and Treatment of Varices During Pregnancy", Schweizerische Medizinische Wochenschrift, 84$^{th}$ year, No. 1, pp. 13–14, Jan. 2, 1954 and translation into English.
G.D. Lilly et al., "An Evaluation of "High" Lumbar Sympathectomy in Arteriosclerotic Circulatory Insufficiency of the Lower Extremities", Surgery, Original Communications, vol. 35, No. 1, pp. 40–44, Jan. 1954.
Maarz, "Nil nocere!: Life–threatening anaphylactic Incidents in Connection with Sclerosing of Varicose Veins", Munchener Medizinische Wochenschrift, vol. 27, No. 35, 1954.
E.J. Orbach, "Allergenic Tissue Reaction of Catgut, an Aid for the Obliteration of Varicose Veins", The Journal of the International College of Surgerons, vol. XXII, No. 6, pp. 707–710, Dec. 1954.
H. Leidinger, Schlerosation with air–block technique (Varicocid plus Varicocid foam), Medizinische Klinik, pp. 1183–1184, 1954 and translation into English.
J and P Vacheron, "Essential Varicose Veins on Lower Limbs: Sclerosant Treatment by Streaming", Archives of Cardio–Vascular Diseases, 7$^{th}$ Year, No. 12, pp. 1033–1038, Dec. 1954 and translation into English.
A. Ree, "Varicose Vein Treatment with Foam of Etamolin", Dansk Laegeforening, No. 12–15, pp. 452–453, Jun. 1955 and translation into English.
A. Hübner, "Der Chirurg, Journal of All Fields of Surgical Medicine", 26$^{th}$ Year of Edition, 1955 with translation into English.
H. Dodd, "The 'Stripping' Operation for Varicose Veins", The Postgraduate Medical Journal, vol. 31, pp. 73–78, 1955.
F. Jaeger, "Primary or Secondary Varicose Veins", Die Medizinische, No. 36, pp. 1237–1340, Sep. 1955 and translation into English.
W. Leun et al., "The Limits and Risks of the Sclerotherapy of Varicose Veins", German Medical Weekly Journal, No. 7, pp. 257–260, Feb. 18, 1955 and translation into English.
F. Schörcher, "For the Practice Varicose Veins and Deep Chronic Crural Thrombosis", Münchener Medizinische Wochenscrift, No. 41, pp. 1354–1358, Oct. 14, 1955 and translation into English.
K. Sigg, "The Treatment of Leg Ulcers", Die Medizinische, No. 17, pp. 646–648, 1955 and translation into English.
K. Sigg, "Therapeutic Issues—On the Treatment of Vein Thrombosis with Butazolidin", Schweizerische Medizinische Wochenschrift, 65$^{th}$ year of the edition, No. 11, pp. 261–262, Mar. 12, 1955 and translation into English.
M.H. Steinberg, "Evaluation of Sotradecol in Sclerotherapy of Varicose Veins", Angiology The Journal of Vascular Diseases, vol. 6, No. 6, pp. 519–532, Dec. 1955.
P. Koistinen, "Eräitä näkökohtia alaraajojen laskimon–laajentumien hoidosta ja ennusteesta", Duodecim, vol. LXXII, No. 12, pp. 1000–1015, 1956.
Flückiger, P., Brugg, "Non–Surgical Retrograde Sclerosis of Varicose Veins With Varsyl Foam," Schweizerische Medizinische Wochenschrift No. 48, pp. 1368–1370, 1956 and translation into English.
R.W. Décoppet, "The Sclerotherapy of Varices with Thrombophilic Patients", Swiss Medical Weekly Journal, 86$^{th}$ year, No. 20, pp. 509–513, May 19, 1956 and translation into English.
R. May, "Impairments and Risks of the Treatment of Varicose Veins", Münchener Medizinische Wochenschrift, No. 1, pp. 13–16, Jan. 1956 and translation into English.
E. Rappert, "The Therapy of Varicose Crural Ulcers", Wiender Medizinische Wochenschrift, vol. 106, No. 48, pp. 999–1000, Dec. 1, 1956 and translation into English.
K. Sigg, "Varicose Veins and Deep Seated Chronic Leg Vein Thrombosis" Münchener Medizinische Wochenschrift, vol. 98, No. 8, pp. 260–263, Feb. 1956.
M.J. Oppenheimer et al., "In vivo Visualization of Intracardiac Structures with Gaseous Carbon Dioxide—Cardiovascular–Respiratory Effects and Associated Changes in Blood Chemistry", *American Journal of Physiology,* vol. 186, pp. 325–334, Jul.–Sep. 1956.
K. Sigg, "Treatment of Superficial and Deep Thrombosis and the Application of Butazolidine", Gynaecologia, Supplementum ad vol. 144, pp. 19–23, Jul. 2 to 4, 1956.
K. Sigg, "A Good Prophylaxis of Thrombosis during Pregnancy, delivery and childbed as well as for Operations can Prevent the Thrombo–Embolism", Munchener Medizinische Wochenschrift, vol. 99, No. 17, p. 581 and 610–613 Apr. 1957 and translation into English.
H. Mayer et al., "Angiology: The Aetiology and Treatment of Varicosities of the Lower Extremity," Chirurgische Praxis, pp. 521–528, 1957 and translation into English.
T. Durant, et al., "The Safety of Intravascular Carbon Dioxide and its Use for Roentgenologic Visualization of Intracardiac Structures", Annals of Internal Medicine, vol. 47, No. 2, pp. 191–210, Aug. 1957.
R.R. Foote, "Varicose Vein Problems in General Practice", The Practitioner—Medical Etiquette, vol. 179, No. 179, pp. 59–66, Jul. 1957.
E.J. Orbach, "Reappraisal of the Sclerotherapy of Varicose Veins", Angiology—The Journal of Vascular Diseases, vol. 8, No. 6, pp. 520–527, Dec. 1957.

E. Rappert, "The treatment of varicose veins following a phlebitis and thromobosis", Winer Medizinische Wochenschrift, No. 4, pp. 100–101, 1957 and translation into English.
G. Savonuzzi et al., "A Therapeutic Method that Combines Sclerosing Agents and Anticoagulants for varicose diseases of the lower limb", Minerva Medical, vol. XLVIII, No. 24, pp. 1124–1126, Mar. 24, 1957 and translation into English.
Von H. Westhues et al., "The Varicose Symptom Complex", Medizinische Klinik, No. 16, pp. 657–660, 1957, and translation into English.
H. Willenegger et al., "Attempt at carrying out Thromboembolism Propylaxis without Anticoagulants", Schweizerische Medizinische Wochenschrift—Journal Suisse de Medecine, vol. 87, Supplement for No. 24, pp. 739–748, 1957 and translation into English.
K. Sigg, "New Approaches to the Treatment of Thrombosis", Angiology—The Journal of Vascular Diseases, vol. 8, No. 1, pp. 44–59, Feb. 1957.
K. Sigg et al., "Prophylaxis of Thrombosis during Gravidity", Die Medizinische, No. 12, pp. 420–423, Jan. 1957 and translation into English.
B. Gyorgy, "Visszérbetegség Másodlagos Szövödményeinek Kelelése", Orvosi Hetilap, vol. XCIX, No. 35, pp. 1215–1218, 1958.
Dr. Hermann Rompp; "Varsyl"; Chemie Lexikon, Vierte Vollig Neu Bearbeitete Auflage; p. 4649; 1958.
F. Jaeger, "Varcose Veins", Deutsche Medizinische Wochenschrift, vol. 83, No. 30, p. 1295, Jul. 1958, and translation into English.
K. Sigg, "Prevention and Treatment of Thromboembolic Complications", Wiener Medizinische Wochenschrift, No. 10, pp. 206–213, Mar. 1958, and translation into English.
E. Rappert, "The achievements of surgical therapy of varicose veins and leg ulcers?", Die Medizinische, No. 22. pp. 906–914, May 1958, and translation into English.
E.J. Orbach, "Has Injection Treatment of Varicose Veins Become Obsolete?", The Journal of American Medical Association, vol. 166., No. 16, pp. 1964–1966, Apr. 19, 1958.
A. Ree; "The Treatment of Varicose Veins with Etamolin Foam"; Acta Dermato–Venereologica; vol. 39, pp. 428–432; 1959.
H. Dodd, "Varicose Veins and Venous Disorders of the Lower Limb", The Irish Journal of Medicinal Science, Sixth Series, No. 400, pp. 162–174, Apr. 1959.
A. I. S. MacPhearson, "The Treatment of Varicose Veins", The Practitioner—Diseases of the Veins, vol. 183, No. 1093, pp. 11–18, Jul. 1959.
F.R. Methiesen, "Subclinical Deep Venous Damage After Sclerosing Injection Demonstrated by Phlebography", Acta Chirurgica Scandinavica, vol. 118, Fasc, 2, pp. 155–166, 1959.
C. Olivier, "Surgical Treatment of Trophic Ulcers of the Inferior Members", Journal de Chirurgie, vol. 78, No. 2, pp. 157–174, Oct. 1959 and translation into English.
K.R. Ramstad et al., "Operative Treatment of Varicose Veins—Follow–up of Patients Treated with ligature/injection and "Stripping" respectively", Tidsskrift for Den Norske Laegeforening, No. 10, pp. 623–625, May 1959.
I. Berson, "Sclerotization or surgery in the treatment of varicose veins of the inferior extremities", University Clinic for dermato–venerology, Lausanne, pp. 485–190, 1960 and translation into English.
J. Marmasse, "Sclerosing Injections in the Saphenofemoral Junction of the Saphenous Veins. Exploration, Injection, Critique.", La Semaine des Hopitaux, vol. 36, No. 17, pp. 1086–1095, Apr. 1960 and translation into English.
F.R. Mathiesen, "Treatment of Varicose Veins—Retrograde Injection or Communicant Resection", Nordisk Medicin, vol. 64, No. 48, pp. 1525–1529, 1960 and translation into English.
P. Sicard, "Sclerosing Treatment of Varicose Veins of the Lower Limbs", Therapeutics, vol. 36, No. 2, pp. 127–129, Feb. 1960 and translation into English.
W. Stern, "Varicose Veins", The Medical Journal of Australia, vol. II, No. 18, pp. 849–852, Oct. 29, 1960.
F. Voss, "Special Methods in the Sclerotherapy of Venous Leg Maladies", Zeitschrift für Haut–und Geschlechts–Krankheiten, vol. XXVII, No. 9, pp. 304–306, 1960 and translation into English.
W.G. Fegan, "Continuous Uninterrupeted Compression Technique of Injecting Varicose Veins", Proceedings of the Royal Society of Medicine, vol. 53, No. 7, pp. 837–840, Jul. 1960.
K. Sigg et al., "New Sclerosing Substances for Varicose Veins", Munchener Medizinische Wochenschrift, Issue 1, Mar. 1961 and translation into English.
J.T. Hobbs, "The Treatment of Varicose Veins in Dublin", Clinical Supplement, pp. 57–60, 1961.
A. Weidmann, "The Varicose Symptom Complex", Report on the Literature from the years 1955–1960, Part 1, Varices, Der Hautarzt, vol. 12, No. 9, pp. 385–391, Sep. 1961 and translation into English.
Von A. Wiedmann, "Varicose Veins", Der Hautarzt, Year 12, No. 10, pp. 433–438, Oct. 1961 and translation into English.
E. Günther, "On the indication and method of sclerotherapy", Ärztliche Fortbildung, vol. 55, Brochure 22, pp. 1296–1298, Nov. 1961 and translation into English.
R. Rauhs, "Sclerotherapy, its indications and treatment successes", Klinische Medizin, Issue 1, pp. 51–2, Jan. 1961 and translation into English.
W. Schneider, "Regarding non–operative varicosclerosation", Die Medizinische Welt, vol. 3, No. 5, pp. 225–227, Feb. 1961 and translation into English.
K. Sigg, "Treatment of Varices, varicose ulcer and thrombosis", Vienna Medical Weekly Journal, No. 6, Feb. 11, 1961 and translation into English.
L. Gerson, "The Treatment of Varicose Veins, A Critical Study of Choice of Method", Angiology, The Journal of Vascular Diseases, vol. 13, No. 16, pp. 260–264, 1962.
W. Maurer, "Is the sclerosing therapy in the case of varicosis advisable in practice?", Therapie der Gegenwart, Issue 5, pp. 242–245, May 1961 and translation into English.
J.P. Medelman, "History of the Section on Radiology", The Journal of the American Medical Association, vol. 178, No. 8, pp. 785–911, Nov. 25, 1961.
H. Dodd, "Varicose Veins and Venous Disorders of the Lower Limb", The Proceedings of the Cardiff Medical Society, pp. 28–45, 1962.
H.O. Schneider, "Varix Treatment with Modern Sclerosing Agent", Zeitschrift Für Haut und Geschelchtskrankheiten, Band XXXIII, Heft No. 5, pp. 163–166, Sep. 1962 and translation into English.
P. Flückiger et al., "Physical and Biological Pathogenetic Components of Varicosis", Schweizer Medizinische Wochenschrift, No. 45, 1963.

E.J. Orbach, "Misconceptions and Pitfalls in Sclerosing Therapy of Varicose Veins", Angiology—The Journal of Vascular Diseases, vol. 14, No. 11, pp. 552–555, Nov. 1963.

O. Gilje, "Injection Treatment of Varicose Veins", Den norske Legeforening, No. 17, pp. 1380–1381, Sep. 1963 and translation into English.

J.C. Luke et al., "Factors in the Improvement of Results in Varicose Vein Surgery", Improved Vein Surgery, Canadian Journal of Surgery, vol. 6, No. 2, pp. 145–148, Apr. 1963.

K. Sigg, "Varicosis and Thrombosis during Pregnancy, birth and in childbed", Zentralblatt für Gynäkologie, No. 8, pp. 254–259, Feb. 23, 1963 and translation into English.

E.C. Emerson, "A Reappaisal of the Injection Treatment of Varicose Veins", Angiology The Journal of Vascular Diseases, vol. 14, No. 1, pp. 8–13, Jan. 1963.

P. Flückiger et al., "A Contribution to the Techniques for Outpatient Treatment of Varicose Veins", Lecture delivered at the meeting of the German Working Group on Phlebology and the Hamburg Dermatological society on Oct. 20, 1962, Med. Welt 1963, No. 12, pp. 617–621.

M. Fabi et al., "Un Nuovo Metodo Di Terapia Sclerosante nel Trattament Delle Varici", L'Arcispedale S. Anna di Ferrera, Book 1, pp. 351–354, 1964.

W. G. Fegan et al., "A Modern approach to the injection treatment of varicose veins and its applications in pregnant patients", American Heart Journal, vol. 68, No. 4, pp. 757–764, Oct. 1964.

H.J. Leu et al., "The Modern Conception of Therapy of Varicose Veins", Angiology, The Journal of Vascular Diseases, vol. 15, No. 9, pp. 371–378, Sep. 1964.

E.J. Orbach, "A Unified Approach to the Therapy of Varicosities", Angiology, vol. 15, No. 12, pp. 558–560, Dec. 1964.

R. Santler, "Sclerosing Therapy of Varicose Veins", Weiner Klinische Wochenschrift, Issue 24, No. 76, pp. 431–434, Jun. 12, 1964 and translation into English.

W. Schneider et al., "On the histology of the Varicose Injection Treatment in People with new Injection Treatment Agents", Archive for Clinical and Experimental Dermatology, vol. 220, pp. 234–249, 1964 and translation into English.

K. Sigg, "Treatment of Varicose Veins in 2–5 days", Dermatologica, vol. 129, No. 2, pp. 111–117, 1964 and translation into English.

K. Sigg, "La Profilassi e la terapia delle malattie venose degli arti inferiori mediante la compressione con fasciature e con calze elastiche", Minerva Ginecologica, vol. 16, No. 19, pp. 817–823, Oct. 15, 1964.

E.J. Orbach, "Article on Treatment of Teleangiectasias", Zentralblatt für Phlebologie, Heft 1, Band 3, pp. 4–7, Feb. 15, 1964 and translation into English.

von H. Pfosi, "On the Sclerosing Treatment of Varicose Veins", Schweizerische Rundschau für Medizin—Revue Suisse de medecine, 54$^{th}$ year of Edition, No. 20, pp. 868–871, Jul. 22, 1965 and translation into English.

K. Sigg, "Varicose Vein Therapy", Deutsche MEdizinische Wochenschrift, No. 15, pp. 665–666, Apr. 9, 1965 and translation into English.

R. Tournay, Indication of the Exclusive Sclerotherapy or the Consecutive Combination Therapy Surgery–Sclerotization of Varicose Veins, Zentralblatt für Phlebologie, vol. 4, No. 1, pp. 133–142, Feb. 15, 1965 and translation into English.

C. Olivier et al., "Reinterventions Performed on Primary Varicose Veins of the Lower Limbs", La Presse Medicale, vol. 74, No. 26, pp. 1355–1360, May 25, 1966 and translation into English.

E.J. Orbach, "The Place of Injection Therapy In the Treatment of Venous Disorders of the Lower Extremity—with Comments on its Technique", Angiology—The Journal of Vascular Diseases, vol. 17, No. 1, pp. 18–23, Jan. 1966.

G. Fegan, "The Treatment of Venous Insufficiency During Pregnancy", Varicose Veins—Compression Sclerotherapy, Chapter VII, pp. 93–98, 1967.

M.D..–D. Bock; "Varicosis and its Therapy"; Ärztliche Praxis; XIX vol., No. 60, pp. 2146–2148; Jul. 29, 1967 and translation into English.

P. Flückiger, "Intraoperative Varicosclerosation with Sodium Tetradecyl Foam in the Babcock Operation", Zentralblatt für Phlebologie, Heft 1, Band 6, pp. 514–518, Feb. 1967 and translation into English.

K. Sigg, "Sclerotherapy in the Treatment of Varicose Veins", Internist, pp. 388–398, 1967 and translation into English.

Dr. E. Lunkenheimer; Letter to Chem. Fabrik Kreussler & Co.; Mar. 20, 1967 and translation into English.

O. Henschel;"Die Varizenverördening—Verördungstherapie mit Aethoxysklerol—Kreussler"; p. 22; 1968 and translation into English.

W.K. Blenkinsopp, "Effect of Injected Sclerosant (Tetradecyl Sulphate of Sodium) on Rat Veins", Angiologica, vol. 5, No. 6, pp. 386–396, 1968.

E. Frugis et al., "Telangieceasia Sclerotherapy of the Lower Limbs", Minerva Dermatologica, Vo. 43, pp. 368–371, 1968 and translation into English.

J. Orbach, "Varicose Veins", Medical Trial Technique Quarterly, vol. XIV, No. 4, pp. 27–38, Jun. 1968.

J. Steinacher et al., "Path and Retention Time of a Contrast Medium in the Superficial Venous System under the Conditions of Varix Obliteration. A Study on the method of varix obliteration", Zsch. Haut–Geschl, vol. 43, No. 9, pp. 369–376, 1968 and a translation into English.

J.T. Hobbs, "The Treatment of Varicose Veins—A Random Trial of Injection–Compression Therapy Versus Surgery", Brit. J. Surg., vol. 55, No. 10, pp. 777–780, Oct. 1968.

H. Eichenberger, "Results of the Sclerotherapy of Varicose Veins with Hydroxypolyaethoxy–Dodecan", Zentralblatt für Phlebologie, vol. 8, pp. 181–183, 1969 and translation into English.

K. Sigg, "Phlebosclerosation; experience and resuls", Der Chirurg, vol. II, No. 40, pp. 487–491, 1969 and translation into English.

W. Gillesberger; "The Equipment of the Dermatologist Wroking in the Field of Phlebology", the Journal for Skin Diseases; vol. 44 (18), pp. 669–674; 1969 and translation into English.

B. Stemmer et al., Phlebologie, vol. 22, No. 2, pp. 151–172, Apr.–Jun. 1969 and translation into English.

G. Wesener, "Morphology and new therapies for starburst varicosis and essential telangiectasia", Berufs–Dermatosen, vol. 17, No. 5, pp. 273–281, Oct. 1969 and translation into English.

W.K. Blenkinsopp, "Choice of Sclerosant: An Experimental Study", Angiologica, vol. 7, No. 3, pp. 182–186, 1970.

K. Holzegel, "On Sclerosing Agents for Varicose Veins", Zentralblatt Für Phlebologie, vol. 9, pp. 43–53, 1970 and translation into English.

B. Stemmer, "Comparison of Common Sclerosing Techniques", Zentralblatt für Phlebologie, vol. 3, pp. 170–176, 1970 and translation into English.

J. Edmonds–Seal et al., "Air Embolism", Anaesthesia, vol. 26, No. 2, pp. 202–208, Apr. 1971.

H.J. Leu et al., "The Combined Surgical–Sclerotic Ambulatory Treatment of Saphenous Varicose Veins", Schweizerische Rundschau für Medizin, vol. 1, No. 61, pp. 1360–1364, Oct. 31, 1972 and translation into English.

K. Sigg, "Technical Details about Inejcting Varices", Med. Klin., vol. 67, No. 27/28, pp. 955–959, 1972 and translation into English.

Z. Salamon, "Sclerosing Agents—Toxicity and Mechanism of Action", Wiadomosci Lekarskie, vol. 26 (19), pp. 1819–1822, 1973 and translation into English.

W.G. Fegan, "Conservative Treatment of Varicose Veins", Progr. Surg. vol. 11, pp. 37–45, 1973.

P. Flückiger, "Der Erythem–Test im Rahmen der präoperativen Varizenuntersuchung", Praktische Hinweise–Practical Advice, vol. 3, No. 2, pp. 198–199, 1974.

E.J. Orbach, "The importance of removal of postinjection coagula during the course of sclerotherapy of varicose veins", VASA, vol. 3, No. 4, pp. 475–477, 1974.

J.T. Hobbs, "Surgery and Sclerotherapy in the Treatment of Varicose Veins", Arch. Surg. vol. 109, pp. 793–796, Dec. 1974.

E.J. Orbach et al., "Investigation of the Different Injection Techniques in the Sclerotherapy of Varicose Veins by Minidose and Differential Pressure Phlebography", VASA, vol. 4, No. 2, pp. 175–183, 1975.

K. Sigg, "Quick Treatment—a modified Method of Sclerotherapy of Varicose Veins", Zur Diskussion gestellt—Open for Discussion, VASA, vol. 4, No. 1, pp. 73–78, 1975.

H.L. Myers, "Injection Therapy for Varicose Veins", The Journal of Family Practice, vol. 3, No. 5, pp. 531–534, 1976.

E.J. Orbach, "Controversies and Realties of Therapy for Varicosis", International Surgery, vol. 62, No. 3, pp. 149–151, Mar. 1977.

J. Hobbs, "Surgery of Sclerotherapy for Varicose Veins", Archs. Surg. Nol. 109, p. 793, 1974.

P. Ouvry et al., "Aétoxisclerol: First Impressions", Phlébologie, vol. 31, No. 2, pp. 75–77, 1978 and translation into English.

D. Reinharez, "Perforating Vein Sclerosis Technique", Ph Phlébologie, vol. 31, No. 2, pp. 69–74, 1978 and translation into English.

K. Sigg et al., "Treating Varices with Sclerotherapy", Langenbacks Arch. Chir., vol. 347, pp. 231–234, 1978 and translation into English.

E.J. Orbach, "Hazards of Sclerotherapy of Varicose Veins—their prevention and treatment of complications", VASA, vol. 8, No. 2, pp. 170–173, 1979.

P. Ouvry et al., "Sclerosant Treatment of Telangiectasias of the Lower Limbs", Phlébologie, vol. 32, No. 4, pp. 365–370, 1979 and translation into English.

P. Ouvry et al., "Le Traitement Sclérosant des Télangiectasies des Membres Inférieurs", Phlébologie, vol. 35, No. 1, pp. 349–359, 1982.

W. DeGroot,"Techniques of Sclerotherapy for Sunburst Venous Blemishes", J. Dermatol. Surg. Oncol. vol. 11, No. 7, pp. 696–704, Jul. 1985.

D.S. Camara et al., "The Hemodynamic Effects of the Sclerosant Sodium Morrhuate in Dogs", Surgery—Gynecology and Obstetrics, vol. 161, No. 4, pp. 327–331, Oct. 1985.

A. Davy et al., "Ostial Incompetence—Sclerosis or Resection?", Phlébologie, vol. 39, No. 1, pp. 35–45, 1986 and translation into English.

M.P. Goldman et al., "Continuing Medical Education (Dermatologic Surgery), Treatment of Telangiectasia: A review", Journal of the American Academt of Dermatology, vol. 17, No. 2, part 1, pp. 167–182, Aug. 1987.

E. Morsiani et al., "Effect of Intravenous and Intreperivenous Injections of Sclerosants (Sodium Tetradecyl Sulfate and Hydroxy Polyethoxy Dodecan) on the Rat Femoral Vein", *Research in Experimental Medicine,* vol. 187, pp. 439–449, 1987.

P. Ouvry et al., "Sclerotherapy of Perforating Veins", Phlébologie, vol. 40, No. 3, pp. 633–641, 1987 and translation into English.

J.T. Hobbs, "Compression Sclerotherapy in Venous Insufficiency", Acta Chir Scand Suppl., vol. 544, pp. 75–80, 1988.

Dr. Med. Jože Baridevic; "Varicosclerozation in Phlebological Practice"; The Journal for Doctors, in Clinic and Practice; XXI vol. No. 3, pp. 126–136; Jan. 11, 1989, and translation into English.

E.L. Bodian et al., "Treatment of Varicose Veins: Modern Concepts and Methods", The Journal of Dermatologic Surgery and Oncology, vol. 15, No. 2, pp. 191–198, Feb. 1989.

M.A. Farina et al., "Outpatient Treatment of Varicose Vein Segments: Two Techniques Compared", Phlébologie, pp. 1070–1071, 1989 and translation into English.

D. Gasparini, "Therapeutic Embolization in Pulmonary Hemorrhage", Radiologica Interventistica, vol. 77, pp. 223–229, 1989 and translation into English.

G. Hauer, "Diagnostic and Surgical Treatment of Varicose Veins", Herz, vol. 14, No. 5, pp. 274–282, 1989 and translation into English.

K.M. Hördegen, "Conconitant Circulatory Problems in the Arteries or immobility in mostly older patients make outpatient treatment of ulcers more difficult", Schweiz. Med. Wschr., vol. 119, No. 37, pp. 1264–1269, 1989 and translation into English.

P.A. Ouvry, "Telangiectasia and Sclerotherapy", J. Dermatol. Surg. Oncoo. vol. 15, No. 2, pp. 177–181, Feb. 1989.

S.N. Vasdekis et al., "Evaluation of non–invasive and invasive methods in the assessment of short saphenous vein termination", Br. J. Surg., vol. 76, pp. 929–932, 1989.

M. Masaki et al., "The destructive effects of sclerosant ethanolamine oleate on mammalian vessel endothelium", Gastroenterologic Japanica, vol. 25, No. 2, pp. 230–235, Feb. 1990.

N. Weindorf et al., "Control of Sclerosis—Treatment for Varicose Veins", Phlébologie, vol. 43, No. 4, pp. 681–689, 1990 and translation into English.

G.P. Goldman, M.D. "Variations on Injection Technique", Sclerotherapy: Treatment of Varicose and Telangiectatic Leg Veins, pp. 274–275, 290, 312–323, 1991.

G. Belcaro et al., "Treatment of Superficial Venous Incompetence with the Savas Technique", Journal des Maladies Vasculaires (Paris), vol. 16, pp. 23–27, 1991.

H.R. Bernbach, "Sclerosing Injections Using the Sigg Method", Phlëbologie, vol. 44, No. 1, pp. 31–36, 1991 and translation into English.

Y.A. Ershov et al., "Variant of an Operation on Enlarged Veins of the Oesophagus and Cardia in Patients with Portal Hypertension Syndrome", Surgery—Monthly Science Practice Journal, Ministry of Health of the Union of Soviet Socialist Republics All–Union Scientific Society of Surgeons, pp. 46–49, Sep. 9, 1991 and translation into English.

M.P. Goldman, "Sclerotherapy Treatment of Varicose and Telangiectatic Leg Veins", Clinical Methods for Sclerotherapy of Varicose Veins, pp. 274–275, 290, 312 and 323, 1991.

J.T. Hobbs, "Varicose Veins", ABC of Vascular Diseases, vol. 303, pp. 707–710, Sep. 21, 1991.

F. Vin, "Echo–Sclerotherapy of the Small Saphenous Vein", Phlébologie, vol. 44, No. 1, pp. 79–84, 1991 and translation into English.

G. Belcaro et al., "Treatment of Superficial Venous Incompetence with a Hemodynamic Technique on an Outpatient Basis: The SAVAS Technique", Vascular Surgery, pp. 32–36, Jan./Feb. 1992.

R. Muller, "The Ambulatory Phlebectomy", Therapeutische Umschau, vol. 49, No. 7, pp. 447–450, 1992 and translation into English.

G.J. Postma, "Ethanolamine Oleate Injection: Therapeutic and Pharmaceutical Aspects", Journal of the Dutch Association of Hospital Pharmacists, 8$^{th}$ Issue 3, pp. 84–91, Sep. 1992 and translation into English.

M. Schadeck, "Sclerotherapy in the Child", Phlébologie, vol. 45, No. 4, pp. 509–512, 1992 and translation into English.

M. Schadeck; "Ultrasound–controlled Sclerotherapy of the Great Saphenous Veins"; Phlébologie; vol. 46, No. 4, pp. 673–682, 1993 and translation into English.

M. Schadeck; "Duplex Controlled Sclerosing Treatment of the Great Saphenous Vein"; Phlebol; vol. 25, pp. 78–82; 1996 and translation into English.

Craig F. Feled, MD, FACEP: "Treatment of all Sizes of Varicose Veins and Spider Veins for Healthy, Beautiful Legs. Mechanism of Action of Sclerosing Agents and Rationale for Selection of a Sclerosing solution"; American Vein Institute; 1996.

"Sulfaproxyline"; The Merck Index, an Encyclopedia of Chemicals, Drugs, and Biologicals, 12$^{th}$ Edition; p. 1527; 1996.

J.R. Cabrera et al.; "Extending the Limits of Sclerotherapy: New Sclerosing Products"; Phlébologie; 50 No. 2; pp. 181–188; 1997 and translation into English.

J. Cabrera Garrido et al. ; "Elargissement de Limites de la Sclérothérapie: Nouveaux Produits Sclérosants"; Phlébologie; vol. 50, No. 2; pp. 181–188 ; 1997.

J. Garcia Mingo, "Venous Sclerosis with Foam 'Foam Medical System'", Revista Españla de Medicina y Ciruia Cosmética, vol. 7, pp. 29–31, 1999 and translation into English.

Robert J. Min; "Transcatheter Duplex Ultrasound Guided Sclerotherapy"; Abstracts from the 13$^{th}$ Annual Congress of the American College of Phlebology; Nov. 10–13, 1999.

J. Cabrera Garrido et al.; "Escleroterapia en Microrespuma: Nuevo Concepto en Escleroterapia. Resultados a Lorgo Plazo."; Revista Panamericana e Flebologia y Lonfologia; No. 34; pp. 29–37; Sep. 1999.

A. Cavezzi, "The Use of Sclerosant Foam in Sclerotherapy: possiblities and limits", Management of Venous Disease in the New Millennium, pp. 16–17, Jul. 2000.

J. Cabrera et al. ;"Treatment of Varicose Long Saphenous Veins with Sclerosant in Microfoam Form: Long–Term Outcomes"; Phlebology; No. 15, pp. 19–23; 2000.

E. Rabe et al.; "Guidelines to Sclerosing Treatment of Varicose Veins", Leitlinien der DGP, Phlebologie; vol. 6, pp. 154–158; 2001 and translation into English.

D. Goldberg ;"Nd : YAG Laser Treatment of Spider Veins"; pp. 284–288; A. Frullini; "Sclerosing Foam with Polidocanol of Sodium Tertradecyl Sulphate in the Treatment of Superficial Venous Insuffiency"; pp. 289–292; J. Cabrera et al.; "Treatment of Varicose Long Saphenous Veins with Sclerosant in Microfoam Form: Long–Term Outcomes"; pp. 293–298. F. Heinrich; "Venous Thrombosis and Pulmonary Embolism during Pregnancy and the Puerperium"; pp. 299–308 F.X. Breu et al. ;"Duplex Scanning of Lipedema and Lymphedema"; pp. 309–320; Scope on Phlebology and Lymphology; vol. 8; Issue 3/4; Dec. 2001.

Gianni Belcaro; "Micro–sclerotherapy"; Sclerotherapy in Venous Disease; pp. 89–95; 2002.

A. Frullini et al., "Sclerosing Foam in the Treatment of Varicose Veins and Telangiectases: History and Analysis of Safety and Complications", Dermatol Surg. vol. 28, No. 1, pp. 11–15, Jan. 2002.

P. Coleridge Smith, "Foam Sclerotherapy in Treatment of Varicose Veins: Results from Europe", Invited Presentation at Pacific Vascular Symposium, Kona, Nov. 2002.

A. Cavezzi et al., "Treatment of Varicose Veins by Foam Sclerotherapy: Two Clinical Series", The Venous Forum of the Royal Society of Medicine and Societas Phelbologica Scandinavica, vol. 17, No. 1, pp. 13–18, Nov. 2002.

Butler Studies to Date, "Summary of the Butler gas physiology studies to date (Jun. 13, 2003)", pp. 1–12.

Syllabus & Scientific Abstracts of the UIP World Congress Chapter Meeting, San Diego, California, Aug. 27–31, 2003.

Dr. J.C. Wollmann et al.; Evaluation of the Test: Kreussler Pharma; pp. 17–28, Jan. 29, 2003 and translation into English.

Dr. A. Wan der Ges. M.b.h.; "Plebocid"; Vienna.

"Ethanmolin, (ethanolamine oleate)", Cypros Pharmaceutical Corporation.

C. Frullini, et al., "Personal Experience with the Sclerosing Foam in Duplex Guided Sclerotherapy", pp. 1–4.

"Phlebocid"; CSST—Service du Répertoire Toxicologique: Case No.:2272–11–9; http://www.reptox.csst.

J. Cabrera; "Application Techniques for Sclerosant in Micro–Foam Form"; pp. 39–44.

Pr. Dr. R. Höhler ; "The Indication of the Rotation Speed and the Duration of the Rotation is not Sufficient for Foams Produced by a Rotating Brush to be Able to Produce a Foam that Has Well–Defined Properties and that Can Be Reproduced."; and translation into English.

Pr. Dr. R. Höhler ; "Comparison Between Three–Dimensional Foams and Two–Dimensional Foams Which Are Produced by Squashing a Three–Dimensional Foam between a Two–Dimensional Foam."; Laboratoire de Physique de Milieux Divisés et Interfaces Université de Marne–la Vallée and translation into English.

A. Frullini; "Sclerosing Foam in the Treatment of Recurrent Varicose Veins"; FoamSclerotherapy—State of Art; pp. 73–77.

* cited by examiner

INJECTABLE MICROFOAM CONTAINING A SCLEROSING AGENT

Matter enclosed in heavy brackets [ ] appears in the original patent but forms no part of this reissue specification; matter printed in italics indicates the additions made by reissue.

This is a continuation of international application Serial No. PCT/ES94/00064, filed Jun. 21, 1994.

PRIOR ART

[Schlerosis] *Sclerosis* of varices is based on injecting liquid substances in them, which causing a localized inflammatory reaction propitiates the elimination of these abnormal veins.

Upon injecting a sclerosing agent, a mixture thereof with the blood contained in the vein is produced and diluted in an unknown proportion. The results are uncertain (due to overdose or underdose) and limited to short varicose segments. As the size of the varices to be injected decreases, the lesser this dilution is and the results that are obtained are more foreseeable. Nowadays, sclerosis is a technique chosen in cases of small and medium-sized varices. Surgery is used for those varices with a diameter equal to larger than 7 mm.

Sclerosis and surgery complement each other at this time, but sclerotherapy continues without being able to be applied to large varicose trunci.

In these large sized varices, upon injecting a sclerosing substance, the concentration thereof in the vein, its homogenous distribution in the blood and the time that it is going to be in contact with the inside walls of the [treted] *treated* vein are unknown.

In 1946 Orbach injected in small caliber varices some few cubic centimeters of air and verified displacement of the blood inside the vessel, which is occupied by the injected air. The sclerosing agent introduced afterwards is more effective than if it has been injected into the blood.

In thick varices, upon injecting air, the described phenomenon of displacement of the blood by the injected air does not take place, but rather this forms a bubble inside the vein that makes the process ineffective in these vessels.

This same author conceived, a few years [late] *later*, injection of foam obtained by agitating in a container containing sodium tetradecyl sulfate, an anionic sclerosing detergent with a high foaming capacity.

The process turns out to be rather useless due to the large-sized bubbles formed and dangerous due to the collateral effects of the atmospheric nitrogen, not very soluble in blood.

Both methods had very little practical repercussion as they were used only in small varices.

DESCRIPTION OF THE INVENTION

This invention refers to the preparation of a sclerosing microfoam.

In accordance with the present invention it has been discovered that injecting in a horizontal position a microfoam of pharmacologically inert sterile physiological serum, it is verified that the microfoam causes displacement of the blood contained in the vessel, even in more developed varices, due to the fact that the pressure of the blood contained in them horizontally is low.

The lifting of the injected member decreases even more the venous pressure, facilitating the exclusive filling of the vein with microfoam; this remaining in the vessel while the patient is not lifted from the examination table.

Upon replacing the prepared microfoam with the physiological serum by microfoam prepared with a sclerosing agent and injecting it in the vein, this displaces the blood that the vein contains and guarantees the contact of the sclerosis agent with the endothelium of the vein, at a known concentration and for a controllable amount of time, achieving sclerosis of the entire occupied segment.

The advantages of this process allow:

1. To know the concentration of the sclerosing agent in the vessel, as the microfoam displaces the blood and is not diluted in it like a liquid in it.

2. To guarantee the homogenous distribution of the product of sclerosis in the inside thereof.

3. To control the time in which it is kept in contact with the inside walls of the vein.

All of these factors are not known exactly nor are they controllable with the use of liquid sclerosing agents.

The elaboration of the present invention is carried out with the preparation of a microfoam with any sclerosing agent, such as: [polydocanol] *polidocanol*, sodium [tetradecly] *tetradecyl* sulfate, hypertonic glucosated or glucosaline solutions, chromated glycerol, ethanolamine oleate, sodium morrhuate, iodated solutions.

Once the sclerosing microfoam has been prepared by any one of the existing processes, two of which will be described hereinafter, it is introduced in any sterile vessel that can be used later to be injected in the vessels to be treated, and that permits the stability of the same, so that it can be removed by a syringe, or by any other instrument that allows injection thereof into the vessels to be treated.

EXAMPLE 1

The preparation of the sclerosing microfoam is done by mixing in a sterile, hermetic container and connected if desired to a bottle under oxygen pressure, mixture of oxygen and carbon *dioxide* or other physiological [gasses] *gases*; mechanical beating is carried out by means of a micromotor that makes an écouvillon submerged in the sclerosing solution to be foamed turn.

Beating between 8,000 and 15,000 rpm, for a time between 60 and 120 seconds, the microfoam is achieved.

This is introduced into any container that can be used for subsequent storage and later injection into the veins to be sclerosed.

In the event that the sclerosing agent does not have a foaming capacity Polysorbate 20, Polysorbate 80, Polygeline or any other substance with a foaming capacity accepted as inert for intravenous use is added to it.

EXAMPLE 2

The sclerosing agent is introduced into a hermetic, pressurized and sterile container and by stirring the solution the microfoam is achieved, with a outlet from the container for its subsequent use.

*The invention can also embrace prepared or extemporaneously prepared injectable microfoam for therapeutic uses characterized in that the microfoam is prepared with any sclerosing substance. In one embodiment, the sclerosing substanc in the injectable microfoam is polidocanol. In another embodiment, it is sodium tetradecyl sulfate. In a further embodiment, it is a hypertonic glucostated or glucosaline solution. In still another embodiment, the scleros-*

*ing substance can be chromated glycerol. The sclerosing substance in another embodiment is ethanolamine oleate. Another embodiment could envisage sodium morrhuate as the sclerosing substance. Still another, envisages any iodated solution.*

*The present invention also uses the inventive microfoam in phlebology. The sclerosing substance in the microfoam can be polidocanol or sodium tetradecyl sulfate.*

*The present invention also uses the inventive microfoam in the treatment of esophageal varices. The sclerosing substance in the microfoam can be polidocanol or sodium tetradecyl sulfate.*

*The present invention also uses the inventive microfoam in a proctology. The sclerosing substance in the microfoam can be polidocanol or sodium tetradecyl sulfate.*

*The present invention also uses the inventive microfoam in angiology. The sclerosing substance in the microfoam can be polidocanol or sodium tetradecyl sulfate.*

What is claimed is:

[1. Prepared or extemporaneously prepared injectable microfoam for therapeutic uses characterized in that the microfoam is prepared with any sclerosing substance.]

[2. Injectable microfoam for therapeutic uses, according to claim 1, characterized in that the sclerosing substance is polydocanol.]

[3. Injectable microfoam for therapeutic uses, according to claim 1, characterized in that the sclerosing substance is sodium tetradecyl sulfate.]

[4. Injectable microfoam for therapeutic uses, according to claim 1, characterized in that the sclerosing substance is a hypertonic glucostated by glucosaline solution.]

[5. Injectable microfoam for therapeutic uses, according to claim 1, characterized in that the sclerosing substance used is chromated glycerol.]

[6. Injectable microfoam for therapeutic uses, according to claim 1, characterized in that the sclerosing substance used is ethanolamine oleate.]

[7. Injectable microfoam for therapeutic uses, according to claim 1, characterized in that the sclerosing substance used is sodium morrhuate.]

[8. Injectable microfoam for therapeutic uses, according to claim 1, characterized in that the sclerosing substance used is any iodated solution.]

[9. A method for phlebologic treatment comprising injecting the microfoam of claim 1 into vessels to be treated.]

[10. A method for phlebologic treatment comprising injecting the microfoam of claim 2 into vessels to be treated.]

[11. A method for phlebologic treatment comprising injecting the microfoam of claim 3 into vessels to be treated.]

[12. A method for treatment of esophageal varices comprising injecting the microfoam of claim 1 into vessels to be treated.]

[13. A method for treatment of esophageal varices comprising injecting the microfoam of claim 2 into vessels to be treated.]

[14. A method for treatment of esophageal varices comprising injecting the microfoam of claim 3 into vessels to be treated.]

[15. A method for proctologic treatment comprising injecting the microfoam of claim 1 into vessels to be treated.]

[16. A method for proctologic treatment comprising injecting the microfoam of claim 2 into vessels to be treated.]

[17. A method for proctologic treatment comprising injecting the microfoam of claim 3 into vessels to be treated.]

[18. A method for angiologic treatment comprising injecting the microfoam of claim 1 into vessels to be treated.]

[19. A method for angiologic treatment comprising injecting the microfoam of claim 2 into vessels to be treated.]

[20. A method for angiologic treatment comprising injecting the microfoam of claim 3 into vessels to be treated.]

*21. An injectable microfoam for therapeutic use that is prepared or extemporaneously prepared comprising*

*at least one sclerosing substance chosen from polidocanol, sodium tetradecyl sulfate, hypertonic glucosated solutions, hypertonic glucosaline solutions, chromated glycerol, ethanolamine oleate, sodium morrhuate, and iodated solutions, and*

*wherein the injectable microfoam is made in a container under pressure of oxygen.*

*22. The injectable microfoam of claim 21, wherein the at least one sclerosing substance is polidocanol.*

*23. The injectable microfoam of claim 21, wherein the microfoam further comprises at least one substance with a foaming capacity.*

*24. The injectable microfoam of claim 23, wherein the at least one substance with a foaming capacity is chosen from polysorbate 20, polysorbate 80, and polygeline.*

*25. An injectable microfoam for therapeutic use that is prepared or extemporaneously prepared comprising*

*at least one sclerosing substance chosen from polidocanol, sodium tetradecyl sulfate, hypertonic glucosated solutions, hypertonic glucosaline solutions, chromated glycerol, ethanolamine oleate, sodium morrhuate, and iodated solutions, and*

*wherein the injectable microfoam is made in a container under pressure of a mixture of oxygen and carbon dioxide.*

*26. The injectable microfoam of claim 25, wherein the at least one sclerosing substance is polidocanol.*

*27. The injectable microfoam of claim 25, wherein the microfoam further comprises at least one substance with a foaming capacity.*

*28. The injectable microfoam of claim 27, wherein the at least one substance with a foaming capacity is chosen from polysorbate 20, polysorbate 80, and polygeline.*

*29. An injectable microfoam for therapeutic use that is prepared or extemporaneously prepared comprising*

*at least one sclerosing substance chosen from polidocanol, sodium tetradecyl sulfate, hypertonic glucosated solutions, hypertonic glucosaline solutions, chromated glycerol, ethanolamine oleate, sodium morrhuate, and iodated solutions, and*

*wherein the injectable microfoam is made under pressure of oxygen in a hermetic container.*

*30. The injectable microfoam of claim 29, wherein the at least one sclerosing substance is polidocanol.*

*31. The injectable microfoam of claim 29, wherein the microfoam further comprises at least one substance with a foaming capacity.*

*32. The injectable microfoam of claim 31, wherein the at least one substance with a foaming capacity is chosen from polysorbate 20, polysorbate 80, and polygeline.*

*33. An injectable microfoam for therapeutic use that is prepared or extemporaneously prepared comprising*

*at least one sclerosing substance chosen from polidocanol, sodium tetradecyl sulfate, hypertonic glucosated solutions, hypertonic glucosaline solutions, chromated glycerol, ethanolamine oleate, sodium morrhuate, and iodated solutions, and*

*wherein the injectable microfoam is made under pressure of a mixture of oxygen and carbon dioxide in a hermetic container.*

*34. The injectable microfoam of claim 33, wherein the at least one sclerosing substance is polidocanol.*

*35. The injectable microfoam of claim 33, wherein the microfoam further comprises at least one substance with a foaming capacity.*

*36. The injectable microfoam of claim 35, wherein the at least one substance with a foaming capacity is chosen from polysorbate 20, polysorbate 80, and polygeline.*

* * * * *